US006028042A

United States Patent [19]

Chambers et al.

[11] Patent Number: 6,028,042

[45] Date of Patent: Feb. 22, 2000

[54] SYNTHETIC BAR COMPRISING HIGH LEVELS OF ALKYLENE OXIDE AS STRUCTURANT PREPARED BY SIMPLE MIX PROCESS

[75] Inventors: John George Chambers; Bryan Stuart Joy, both of Merseyside, United Kingdom; Melissa Iva Katz, New York; John Gerrard Sheehan, Brooklyn, both of N.Y.

[73] Assignee: Lever Brothers Company, New York, N.Y.

[21] Appl. No.: 09/052,435

[22] Filed: Mar. 31, 1998

Related U.S. Application Data

[63] Continuation-in-part of application No. 08/594,363, Jan. 30, 1996, abandoned, which is a continuation of application No. 08/213,287, Mar. 15, 1994, abandoned.

[51] Int. Cl.[7] .............................. A61K 7/50; C11D 17/00

[52] U.S. Cl. .......................... 510/155; 510/130; 510/152; 510/153; 510/154

[58] Field of Search .................................... 510/130, 152, 510/153, 154, 155

[56] References Cited

U.S. PATENT DOCUMENTS

| | | | |
|---|---|---|---|
| 2,987,484 | 6/1961 | Lundberg et al. . | |
| 3,687,855 | 8/1972 | Halpern . | |
| 4,169,067 | 9/1979 | Joshi | 510/152 |
| 4,335,025 | 6/1982 | Barker et al. | 252/550 |
| 4,612,136 | 9/1986 | Novakovic et al. . | |
| 4,673,525 | 6/1987 | Small et al. | 252/132 |
| 4,696,767 | 9/1987 | Novakovic et al. . | |
| 5,225,097 | 7/1993 | Kacher et al. | 510/152 |

FOREIGN PATENT DOCUMENTS

| | | |
|---|---|---|
| 479695 | 12/1965 | Nauru . |
| 783223 | 9/1955 | United Kingdom . |
| 1294754 | 11/1972 | United Kingdom . |
| 92/13060 | 6/1992 | WIPO . |

*Primary Examiner*—Necholus Ogden
*Attorney, Agent, or Firm*—Ronald A. Koatz

[57] ABSTRACT

A detergent composition which is suitable for making into bars for personal washing comprises:

(a) 10 to 60% wt. of a synthetic, non-soap detergent;

(b) 20 to 60% wt. of water soluble material which is neither soap nor a non-soap detergent and which has a melting point in the range 40° C. to 100° C.; and (c) 5 to 50% wt. of water insoluble material which is neither soap nor a non-soap detergent and which has a melting point in the range 40° C. to 100° C. The content of water, if any does not exceed 20% wt. of the composition and better is less than 15% wt. The materials (b) and (c) serve to give structure to the bars. The compositions can be prepared by melting together the above mentioned components at a temperature of 50–100° C., without the conventional energetic working. Desirably the molten mixture contains less than 20% wt. material, other than synthetic, non-soap detergent, which does not enter the liquid phase. The melt can be cast into bars or cooled, milled, plodded and stamped into bars.

18 Claims, No Drawings

SYNTHETIC BAR COMPRISING HIGH LEVELS OF ALKYLENE OXIDE AS STRUCTURANT PREPARED BY SIMPLE MIX PROCESS

RELATED APPLICATIONS

The present application is a Continuation-in-Part of U.S. Ser. No. 08/594,363 now abandoned, filed Jan. 30, 1996, which in turn is a Continuation of U.S. Ser. No. 08/213,287, filed Mar. 15, 1994 now abandoned.

FIELD OF THE INVENTION

This invention relates to synthetic detergent bars and detergent compositions which can be shaped into bars.

BACKGROUND

Washing bars can be classified into soap bars, mixed active bars containing a significant proportion of soap and thirdly synthetic detergent bars containing only a small proportion of soap or none at all.

Conventional soap bars comprise a large proportion, typically 60–80% by weight, of fatty acid soap. Fatty acid soaps are selected to provide a balance of soluble and insoluble soaps which provide the required functional properties as regards lather formation and bar structure. Conventional soap bars are manufactured by milling, plodding and stamping a semi-solid mass of soap and other components.

Bars are known which contain a mixture of soap and synthetic detergent where the amount of soap may be less than the amount of synthetic detergent but is nevertheless still a significant contributor to the content of the bar. In such bars, as in conventional soap bars, the content of soap, especially the insoluble soap, contributes to the structure and physical properties of the bar.

The third category is synthetic detergent bars, often known as "Syndet" bars, in which there is no soap or only a small amount and the detergent active is mostly or wholly a synthetic, non-soap, detergent. Generally such bars contain a substantial proportion of material which is not a detergent and which serves to give structure to the bar. Such "structurants" are normally water-insoluble and include such materials as starch and kaolin. The bars frequently also contain a plasticiser: known plasticisers include stearic acid and cetyl alcohol. Known surfactants for Syndet bars include primary alkyl sulphates, alkyl ether sulphates, betaines, sarcosinates, sulphosuccinates and isethionates. These syndet bars containing no soap or only a small proportion of soap are traditionally produced by energetic working of a physical mix of structurant, plasticiser and surfactant, i.e., both the soluble and insoluble components, in a high shear mixer to an end point at which the product is not gritty. The mix is then formed into 'syndet' bars.

The known process has several disadvantages in that the physical mixing step is performed batchwise and requires an energetic mixer.

We have now found that by adopting a novel composition, syndet bars may be produced by a process which dispenses with the known energetic working step.

In contrast with prior compositions and processes, the invention relies on ingredients which are molten at conveniently accessible temperatures but which are above the temperatures normally encountered during use of "Syndet" bars. As a result the necessary intimate mixing of the ingredients of the bar can be accomplished by simple mixing while the bar composition is liquid rather than by relying on energetic working to achieve intimate mixing of a mixture of solids.

The present invention further recognizes that it is only a specific class of water-soluble structurants, i.e., those having defined minimum melting points, which can function to partially replace hydrophobic fatty acid structurants normally used in bar structuring.

If the melting temperature is too low, the composition will be too "liquidy", extruded bar product will be extremely soft and during refining stage, rather than typical "noodles", large sticky balls will typically form. Yield stress measurements show extremely soft and essentially, from a consumer perspective, useless bar.

If, on the other hand, melting point were too high, the bars would be too sticky to process, have low lather and low dissolution.

In short, the water-soluble structurant must be chosen precisely so as to be not too liquidy, so as to be hard enough to process well, yet not be so hard as to form sticky product which will clog machinery and inhibit processing.

It has never been previously recognized that large amounts (i.e., 20% or greater) of specific water-soluble material (e.g., alkylene oxides) could be used for this purpose because there was no recognition that minimum melting point (i.e., MW) was required. Water soluble materials such as alkylene glycols in the art have traditionally been viewed as "moisturizing" ingredients and the materials used would be generally perceived by the art to be liquidy and to not process well.

U.S. Pat. No. 4,812,253 to Small et al., for example, discloses a composition comprising surfactant (component (a) of the subject invention), water-insoluble structurant such as fatty acid (component (c)) and water (component (d)). Although Small et al. mentions that polyalkylene glycol can be used as "moisturizer/emollient" at levels of 10–40% by wt., there is nothing in this reference teaching or suggesting the melting point or MW be above certain minimum levels (i.e., 40° C. and up, preferably 47°–100° C., more preferably 50° to 100° C.).

Indeed, there are no examples of such "moisturizer" at all and preferred moisturizers are said to be coco and tallow fatty acids. As noted, previous art would not have used high levels of alkylene oxides as structurants because they would have believed the bar was unprocessable or, if processable, would create soft, mushy bars of very low yield strength. Nothing in this or any other reference would have motivated the inclusion of specifically defined water-soluble structurants of the invention.

BRIEF SUMMARY OF THE INVENTION

Accordingly, the present invention provides a detergent composition which is, or can be shaped into, a synthetic detergent bar, the composition comprising:

(a) 10 to 60% by weight of a synthetic, non-soap detergent, (b) 10 to 60%, preferably 20 to 60% by weight of a water-soluble structurant which is neither soap nor a non-soap detergent and which has a melting point in the range 40° to 100° C., preferably 47° C. to 100° C., more preferably about 50° C. and greater to 100° C., (c) 5 to 50% by weight of a water-insoluble structurant which is neither soap nor a non-soap detergent and which has a melting point in the range 40° to 100° C., and (d) 1 to 20% by weight water, preferably 1% to 14%, more preferably 3% to 12%, more preferably 4% to 11% and most preferably 5 to 10%.

It is desirable that the content (if any) of material other than said synthetic non-soap detergent (a) which does not melt below 100° C. is less than 20% by weight of the composition.

In many embodiments of this invention the content of the synthetic detergent (a) will lie in the range 10 to 50% by weight. Preferably the composition will contain some water, in an amount from 1% to 14% or 15%, preferably 3% to 12%, more preferably 4% to 10%, and most preferably 5% to 10%.

It will be seen from the above, that a significant constituent of a composition according to this invention is a water-soluble material which melts at a temperature in the range 40–100° C., preferably above 46°, i.e., 47° to 100° C., and serves as a bar structurant. Such a material assists in giving the desired properties notably that the bar has a rigid solid form.

It is also be noted from the above that the composition of the bar can tolerate the presence of some material which does not melt at temperatures below 100° C. Such material can also serve as a structurant. Such material is not an essential requirement and it may be entirely absent. If such material is present, the molten composition will not be fully liquid at temperatures of up to 100° C. unless the non-melting material dissolves in the other materials present. We have found that a moderate amount of material which does not melt can be dispersed in the molten composition while it remains sufficiently liquid to be stirred without requiring energetic working. As will be mentioned again below, this material which disperses but does not melt may be at least part of the non-soap synthetic detergent (a) and/or material other than this category.

Suitable synthetic detergents (a) are: alkyl ether sulphates; alkyl ethoxylates; alkyl glyceryl ether sulphonates; alpha olefin sulphonates; acyl taurides; methyl acyl taurates; N-acyl glutamates; acyl isethionates; anionic acyl sarcosinates; alkyl phosphates; methyl glucose esters; protein condensates; ethoxylated alkyl sulphates; alkyl polyglycosides; alkyl amine oxides; betaines; sultaines; alkyl sulphosucinates, dialkyl sulphosuccinates, acyl lactylates and mixtures thereof. The above-mentioned detergents are preferably those based upon $C_8$ to $C_{24}$, more preferably those based upon $C_{10}$ to $C_{18}$, alkyl and acyl moieties.

For many embodiments of this invention, the amount of synthetic detergent (a) may lie in the range from 10 to 50% wt. Further preferences are at least 20% and not more than 40%.

Amongst the above synthetic detergents, some, notably acyl isethionates are less water-soluble than others. If a detergent of low solubility is used, it is preferably mixed with another synthetic detergent. Thus detergent compositions of this invention may possibly exclude acyl isethionate from the synthetic detergent (a) or may possibly include it jointly with other synthetic detergent. In some embodiments of this invention acyl isethionate is not more than 10% by weight of the composition e.g., 5% to 9.5%. However, further embodiments of the invention include larger quantities of acyl isethionate, e.g., up to 30% by weight of the composition.

The water-soluble structurant (b) is required to melt in the temperature range from 40° C. to 100° C. so that it can be melted to form the bar composition but will be in a solid state at temperatures at which the bar will be used. Preferably it has a melting point of at least 50° C., notably in the narrower range from 50° C. to 90° C.

Materials which are envisaged as the water-soluble structurant (b) are moderately high molecular weight polyalkylene oxide or polyalkylene oxides of appropriate melting point and in particular polyethylene glycols or mixtures thereof.

Polyethylene glycols (PEGs) which are used may have a molecular weight in the range 1500–10,000. In particular, these correspond to PEGs having melting point from about 47° (PEG 1450 has MP of 43–46° C.) to about 70° C. In some embodiments of this invention, however, it is referred to include a fairly small quantity of polyethylene glycol with a molecular weight in the range from 50,000 to 500,000, especially molecular weights of around 100,000. Such polyethylene glycols have been found to improve the wear rate of the bars. It is believed that this is because their long polymer chains remain entangled even when the bar composition is wetted during use.

If such high molecular weight polyethylene glycols (or any other water-soluble high molecular weight polyalkylene oxides) are used, the quantity is preferably from 1% to 5%, more preferably from 1% to 1.5% to 4% or 4.5% by weight of the composition. These materials will generally be used jointly with a larger quantity of other water-soluble structurant (b) such as the above mentioned polyethylene glycol of molecular weight 1500 to 10,000.

Some polyethylene oxide polypropylene oxide block copolymers melt at temperatures in the required range of 40° to 100° C. and may be used as part or all of the water soluble structurant (b). Preferred here are block copolymers in which polyethylene oxide provides at least 40% by weight of the block copolymer. Such block copolymers may be used, in mixtures with polyethylene glycol or other water soluble structurant.

Preferably the total quantity of water soluble structurant (b) is from 20% to 50% by weight of the composition.

The water insoluble structurants (c) are also required to have a melting point in the range 40°–100° C., more preferably at least 50° C., notably 50° C. to 90° C. Suitable materials which are particularly envisaged are fatty acids, particularly those having a carbon chain of 12 to 24 carbon atoms. Examples are lauric, myristic, palmitic, stearic, arachidic and behenic acids and mixtures thereof. Sources of these fatty acids are coconut, topped coconut, palm, palm kernel, babassu and tallow fatty acids and partially or fully hardened fatty acids or distilled fatty acids. Other suitable water insoluble structurants include alkanols of 8 to 20 carbon atoms, particularly cetyl alcohol. These materials generally have a water solubility of less than 5 g/liter at 20° C.

The relative proportions of the water soluble structurants (b) and water insoluble structurants (c) govern the rate at which the bar wears during use. The presence of the water insoluble structurant tends to delay dissolution of the bar when exposed to water during use and hence retard the rate of wear.

Preferably the total quantity of component (c) is from 5% to 50%, more preferably 10% to 40% by weight of the composition.

A water insoluble material which does not melt below 100° C. can function as an additional bar structurant. it may be stipulated as a requirement that the content (if any) of water insoluble material which does not melt below 100° C. is less than 20% by weight of the composition.

If a water insoluble structurant (c) which doses not melt below 100° C. is present it may well be selected from plant materials or minerals. Starches, including corn starch, are preferred amongst the plant materials while kaolin and calcite are preferred mineral materials. The ratio of water soluble structurant (b) to the total of water insoluble structurants may possibly lie in a range from 2:3 or 1:1 up to 3:1 or 5:1.

Some soap, that is to say slats of monocarboxylic fatty acids having chain lengths of 8 to 22 carbon atoms may be included in the bar compositions of this invention. The amount is desirably not greater than 10% by weight of the composition.

We have found that if water insoluble soap is included, it is advantageous in reducing the wear rate of the bars. Such water insoluble soaps are salts of saturated fatty acids having chain lengths of 16 to 22 carbon atoms, especially 16 and 18. Preferably these salts are sodium salts. They melt at temperatures above 100° C. and therefore come within a category (e) which is material, other than synthetic detergent, melting above 100° C.

If water insoluble soap is present in the composition, the amount of it desirably does not exceed 10% by weight of the composition, for example lying in a range from 3% to 9.5% by weight, more preferably 5% to 9%.

It is preferred to include a combination of polyethylene glycol with molecular weight 50,000 to 500,000 as at least part of the soluble structurant (b) and water insoluble soap as at least part of the insoluble material (c). Use of these materials in combination has been found to improve wear rate of the bars, while also giving them a good feel when handled during use.

When such a combination of materials is used, the preferred amounts, by weight of the composition are: 4 to 9.5% of water insoluble soap and 1.5 to 4.5% polyethylene glycol with molecular weight in the range from 50,000 to 500,000.

Materials which may be included but which do not melt at temperatures below 100° C. can be classified as non-soap synthetic detergent which does not completely liquefy at temperatures below 100° C., for example acyl isethionates;

soap, especially water insoluble soap, which does not melt below 100° C.;

other water insoluble materials which do not melt below 100° C.

Materials, other than synthetic detergent, which are water soluble but do not melt below 100° C. are preferably absent, or present only in quantities which are small such as not more than 10%, better not more than 5% by weight of the composition.

It is desirable that the total quantity of material in the second and third of these categories (i.e., materials other than non-soap synthetic detergent) is not more than 20% by weight of the composition. The total quantity of material which does not melt below 100° C. should not exceed 50% by weight of the composition, preferably less, such as not more than 40% or not more than 30%, or even 20% and should not be so much that the molten composition ceases to be stirrable.

Bar compositions of this invention will usually contain water, but the amount of water is only a fairly small proportion of the bar. Larger quantities of water reduce the hardness of the bars. Preferred is that the quantity of water is not over 15% by weight of the bars, e.g., lying in a range from 1 to 14.5%, more preferably 3 to 14% or 3 to 12%, more preferably 4 to 11% and most preferably 5 to 10% by wt.

Bars of this invention may optionally include so-called benefit agents—materials included in relatively small proportions which confer some benefit additional to the basic cleansing action of the bars. Example of such agents are: skin conditioning agents, including emollients such as fatty alcohols and vegetable oils, essential oils, waxes, phospholipids, lanolin, anti-bacterial agents and sanitizers, opacifiers, pearlescers, electrolytes, perfumes, sunscreens, fluorescers and coloring agents. Preferred skin conditioning agents comprise silicone oils, mineral oils and/or glycerol.

According to a further aspect of the present invention there is provided a process for the manufacture of synthetic detergent bars which comprises the steps of:

(i) preparing a liquid mixture of the synthetic, non-soap detergent, the structurants and optionally water at a temperature of 50° C. to 100° C., preferably 50° C. to 90° C., said mixture comprising less than 20% wt. of material other than synthetic non-soap detergent which does not enter the molten liquid phase, (ii) cooling the product of step (i) to a temperature at which it solidifies, and (iii) forming the product of step (i) into bars.

The liquid mixture can be a single or multiple phase system. The single phase can be an isotropic mixture whereas the multiple phase system can comprise either an emulsion or liquid crystal dispersion. The mixture can be prepared by mixing of the components followed by heating of the mixture to the molten state when further mixing will occur, or by heating of the components followed by mixing of the components.

Step (i) may be carried out in a stirred, heated vessel.

For a composition which contains fatty acid or a mixture of soap and fatty acid and also contains polyalkylene oxide, a useful procedure begins with melting the fatty acid in a heated vessel with a stirrer. The stirrer is started, and the polyalkylene oxide is added. At this stage any soap is made in situ by partial neutralization of the fatty acid.

Next the non-soap detergent is added. The end result is a macroscopically homogenous molten mixture, with not more than 50% solids present.

preferably step (ii) is carried out on a chilled, scraped roller which may be part of a chilled mill.

Minor ingredients and benefit agents can be added at this stage, between steps (ii) and (iii).

Step (iii) can comprise milling, plodding and stamping, or optional milling followed by compression of the material into a bar shape.

In an alternative embodiment of the invention, the liquid mixture from step (i) is cast into molds. The casting step can be employed to form a log which is further processed into bars or to form bars directly. Where the product is cast into bars the process steps (ii) and (iii) are combined; the molds which are used can form the final packaging of the bars or the bars can be extracted from the molds and re-packaged.

In order that the present invention may be further understood it will be described with reference to the following illustrative examples. The examples are not intended to be limiting in any way. Unless noted otherwise, the percentages are intended to be percentages by weight.

EXAMPLES

Example 1

Components as listed in Table 1 below were melted together at 80° C. to produce a material consisting predominantly of a liquid phase. All amounts are given in percentages by weight. On cooling to room temperature, solid, generally cubed bars were formed from compositions (A) and (B) using a single bar press. Identical compositions were also formed into bars by using a casting process from the hot melt.

TABLE 1

| | A | B |
|---|---|---|
| SLES 3EO* | 21% | 21% |
| Stearic Acid | 10% | 20% |
| Cetyl alcohol | 10% | — |
| PEG 4000** | 50% | 50% |
| Water | 8% | 8% |
| Perfume | 1% | 1% |

*SLES 3EO denotes sodium lauryl ether sulphate with average 3 ethylene oxide residues.
**PEG 4000 denotes polyethylene glycol with mean molecular weight 4000.

Both the melt-cast and pressed bars had acceptable properties for 'syndet' bars.

Example 2

The material listed in Table 2 below, where all amounts are given as percentages by weight, were melted together at 80° C. to produce a pumpable, stirrable liquid. The liquid melt was poured into bar shaped molds and allowed to cool to form solid bars, i.e., the bars were cast from the melt. Acceptable bars were obtained.

TABLE 2

| | 2A | 2B | 2C | 2D |
|---|---|---|---|---|
| Aerosol OT* | 21 | 45 | 25 | 50 |
| PEG 4000 | 37 | 25 | 37.5 | 25 |
| Stearic Acid | 37 | 25 | 37.5 | 25 |
| Water | 5 | 5 | 0 | 0 |

*Aerosol TO is dioctylsulphosuccinate.

Example 3

The materials listed in Table 3 below were melted together at 80° C. to produce a pumpable, stirrable liquid. All amounts are given in percentages by weight. The liquid melt was cast into bars as in Example 2.

A quantity of each melt was processed into bars by a different route. The melt was cooled by passing over a chilled three-roll mill. Small quantities of perfume, opacifier and flourescer were added, totaling less than 2% by weight of the composition. The resulting composition was re-milled, passed through a vacuum plodder and stamped into the desired bar shape using a manual press.

TABLE 3

| | 3A | 3B | 3C | 3D |
|---|---|---|---|---|
| SLES 3EO | 14 | 21 | 28 | 14 |
| PEG 4000 | 40 | 35 | 30 | 53 |
| Stearic Acid | 40 | 35 | 30 | 27 |
| Water | 6 | 9 | 12 | 6 |

Acceptable bars were obtained by both processing routes.

Example 4

Components as listed in Table 4 below were made into bars by the procedure of Example 2. All amounts are given in percentages by weight. These bars contained a mixture of two detergent actives.

TABLE 4

| | 4A | 4B | 4C | 4D | 4E | 4F | 4G | 4H | 4J | 4K | 4L | 4M | 4N | 4P | 4Q | 4R |
|---|---|---|---|---|---|---|---|---|---|---|---|---|---|---|---|---|
| SLES 3EO | 27 | 20 | 14 | 27 | 2 | 14 | 27 | 20 | 14 | 27 | 20 | 14 | 7 | 20 | 17 | 10 |
| Aerosol TO | 4 | 3 | 2 | — | — | — | — | — | — | — | — | — | 10 | 30 | 25 | 15 |
| Tallow 20EO* | — | — | — | 4 | 3 | 2 | — | — | — | — | — | — | — | — | — | — |
| DEFI** | — | — | — | — | — | — | 4 | 3 | 2 | — | — | — | — | — | — | — |
| CAPB*** | — | — | — | — | — | — | — | — | — | 4 | 3 | 2 | — | — | — | — |
| PEG 4000 | 38 | 46 | 52 | 38 | 46 | 52 | 38 | 46 | 52 | 38 | 46 | 52 | 56 | 20 | 25 | 20 |
| Stearic Acid | 19 | 23 | 26 | 19 | 23 | 26 | 19 | 23 | 26 | 19 | 23 | 26 | 24 | 20 | 25 | 50 |
| Water | 12 | 8 | 6 | 12 | 8 | 6 | 12 | 8 | 6 | 12 | 8 | 6 | 3 | 10 | 8 | 5 |

*Fatty alcohol with mixed 16 and 18 carbon atom chain lengths, ethoxylated with an average of 20 ethylene oxide residues.
**Directly esterified fatty acyl isethionate, which is a mixture containing about 70% by weight of fatty acyl isethionate, 15–20% fatty acid and small quantities of other materials, ex. Lever Brothers, USA.
***Cocoamidopropyl betaine, ex. Albright and Wilson, UK.

Example 5

The materials listed in Table 5 below were made into bars by the procedure of Example 2. All amounts are given in percentages by weight. In these bars, the water soluble structurant was a mixture of polyethylene glycol and a block copolymer of polyethylene oxide and polypropylene oxide, available as Pluronic F87, ex. BASF Germany.

TABLE 5

| | 5A | 5B |
|---|---|---|
| Aerosol OT | 21 | 45 |
| PEG 4000 | 20 | 20 |
| Pluronic F87 | 17 | 5 |
| Stearic Acid | 37 | 25 |
| Water | 5 | 5 |

Example 6

The materials listed in Table 6 below were melted together at 80° C. All amounts are given in percentages by weight.

The PEG 4000 and stearic acid were the first materials to be heated and melted. When these were molten, a small quantity of sodium hydroxide was added to neutralize a little of the stearic acid to sodium stearate. After this the remaining materials were added and stirred to produce a pumpable, homogeneous liquid.

Each melt was cooled by passing over a chilled three-roll mill. 1% of perfume, and 0.3% of titanium dioxide as opacifier were then added, followed by milling and plodding the resulting composition and stamped into the desired bar shape using a manual press.

TABLE 6

| | 6A | 6B | 6C | 6D |
|---|---|---|---|---|
| SLES 3EO | 11 | 11 | 10 | 10 |
| DEFI | 18 | 33 | 20 | 20 |
| CAPB | 1 | 5 | 1 | 1 |
| PEG 4000 | 35 | 25 | 36 | 36 |
| PEG 100,000 | 4 | 4 | 0 | 8 |
| Stearic Acid | 22 | 13 | 20 | 20 |
| Sodium Stearate | 4 | 4 | 8 | 0 |
| Water | 5 | 5 | 5 | 5 |

Example 7

The materials listed in Table 7 below were made into bars by the procedure of Example 3 in which the melt was cooled on a mill, plodded and stamped into bars. All quantities are given as percentages by weight. These bars contained a mixture of three detergent actives.

TABLE 7

| | 7A | 7B | 7C | 7D | 7E | 7F |
|---|---|---|---|---|---|---|
| SLES 3EO | 10 | 9.56 | 9.22 | 10.42 | 9.96 | 9.6 |
| DEFI | 17 | 16.2 | 15.68 | 31.26 | 29.87 | 28.83 |
| CAPB | 1 | 0.96 | 0.92 | 4.72 | 4.53 | 4.37 |
| PEG 4000 | 33 | 31.53 | 30.43 | 23.68 | 22.63 | 21.84 |
| PEG 100,000 | 4 | 3.82 | 3.69 | 3.8 | 3.62 | 3.5 |
| Stearic Acid | 21 | 20.1 | 19.37 | 12.32 | 11.77 | 11.36 |
| Sodium Stearate | 4 | 3.82 | 3.69 | 3.8 | 3.62 | 3.5 |
| Water | 10 | 14 | 17 | 10 | 14 | 17 |

Compositions 7C and 7F gave compositions which were too soft to process whereas the remaining compositions could be processed into firm bars.

Example 8

A number of compositors from the preceding examples were assessed for mildness using a zein test generally as described by Gotte, Proc. Int. Cong. Surface Active Subs., 4th, Brussels, 3, 89–90 (1964). The test determines the amount of amino acid solubilized from zein under specified conditions. The solubilized material is determined by a nitrogen assay. The results were as follows;

TABLE 8

| Composition Number | Solubilized Nitrogen |
|---|---|
| 3A | 0.08 |
| 3B | 0.13 |
| 3C | 0.16 |
| 4D | 0.11 |
| 4G | 0.1 |
| 4K | 0.11 |
| 6A | 0.12 |
| 6C | 0.05 |
| 6D | 0.05 |
| 7D | 0.2 |
| 80/20 Coconut/Tallow Soap | 0.73 |
| 'DOVE' Commercial 'Syndet' Bar Based on DEFI | 0.22 |

The low values of zein solubilization for the bars of this invention indicate very good mildness.

Examples 9–13

In order to demonstrate the criticality of using alkylene glycol of minimum melting point (when using 20% or greater alkylene glycol), applicants prepared the following example 9 to 13 and comparative 1–4:

TABLE 9

| Material | Control | Ex. 9 | Ex. 10 | Comp. 1 | Comp. 2 | Comp. 3 | Comp. 4 | Ex. 11 | Ex. 12 | Ex. 13 |
|---|---|---|---|---|---|---|---|---|---|---|
| Sodium Cocyl Isethionate | 50.59 | 27.00 | 27.00 | 27.00 | 27.00 | 27.00 | 27.00 | 27.00 | 27.00 | 27.00 |
| PEG 8000 | — | 20.90 | 25.90 | — | — | — | — | — | 10.00 | 9.30 |
| Stearic Acid/Coconut Fatty Acid | 23.40 | 20.00 | 20.00 | 20.00 | 20.00 | 20.00 | 20.00 | 17.00 | 17.00 | 17.00 |
| Sodium Stearate | 2.95 | 8.00 | 8.00 | 8.00 | 8.00 | 8.00 | 8.00 | 6.00 | 6.00 | 6.00 |
| Cocamidopropyl Betaine | 2.63 | 4.36 | 4.36 | 4.36 | 4.36 | 4.36 | 4.36 | 4.36 | 4.36 | 4.36 |
| Water (Nominal) | 5.24 | 5.00 | 5.00 | 5.00 | 5.00 | 5.00 | 5.00 | 5.00 | 5.00 | 5.00 |
| Sodium Isethionate | 4.93 | 7.10 | 2.10 | 7.10 | 7.10 | 7.10 | 7.10 | 2.10 | 2.10 | 2.10 |
| PEG 1450 | — | 2.95 | 2.95 | 25.90 | — | — | — | 2.95 | 8.00 | 7.44 |
| PEG 300 | — | 2.05 | 2.05 | — | 25.90 | — | — | 2.05 | 2.00 | 1.86 |
| PEG 600 | — | — | — | — | — | — | 25.90 | — | — | — |
| PEG 1000 | — | — | — | — | — | 25.90 | — | — | — | — |
| PEG 3350 | — | — | — | — | — | — | — | 21 | — | — |
| PEG 4000 | — | — | — | — | — | — | — | — | 7.00 | 6.51 |
| Maltodextrin | — | — | — | — | — | — | — | 10.00 | 10.00 | 6.00 |
| Neat Soap | 6.99 | — | — | — | — | — | — | — | — | — |

TABLE 9-continued

| Material | Control | Ex. 9 | Ex. 10 | Comp. 1 | Comp. 2 | Comp. 3 | Comp. 4 | Ex. 11 | Ex. 12 | Ex. 13 |
|---|---|---|---|---|---|---|---|---|---|---|
| Perfume | 1.00 | 1.00 | 1.00 | 1.00 | 1.00 | 1.00 | 1.00 | 1.00 | 1.00 | 1.00 |
| NaCl | 0.58 | 0.88 | 0.88 | 0.88 | 0.88 | 0.88 | 0.88 | 0.88 | 0.88 | 0.88 |
| $TiO_2$ | 0.15 | 0.70 | 0.70 | 0.70 | 0.70 | 0.70 | 0.70 | 0.70 | 0.70 | 0.70 |
| EDTA | 0.02 | 0.03 | 0.03 | 0.03 | 0.03 | 0.03 | 0.03 | 0.03 | 0.03 | 0.03 |
| EHDP | 0.02 | 0.03 | 0.03 | 0.03 | 0.03 | 0.03 | 0.03 | 0.03 | 0.03 | 0.03 |

As noted, Examples 9 (same formulation for 9, 9*a* & 9B except for water levels) and 10 were made using about 21% and 26% PEG 8000, respectively; Example 11 uses about 22% PEG 3350; and Examples 12 and 13 used combinations of PEG 8000 and PEG 4000. The comparatives were made using about 26% PEG 1450, PEG 300, PEG 600 and PEG 1000.

The following table indicates the melting points of the PEG used in the Examples.

PEG Melting Points

| PEG | Melting Point (C) |
|---|---|
| 300 | −15 to −8 |
| 600 | 20 to 25 |
| 1000 | 37 to 40 |
| 1450 | 43 to 46 |
| 3350 | 54 to 58 |
| 4000 | 59 |
| 8000 | 60 to 63 |

Based on these differences the following processing data were obtained:

It can be seen that, all bars using PEG below PEG 1450 (i.e., corresponding to melting temperatures of about 46° C. and lower), had much lower plodding rates (were not hard enough to extrude), and lower yield stress (indication of bar softness). These bars also generally showed "surging" during plodding, an indication of the bar being too liquid and inadequate for processing.

By contrast, when PEG having higher melting point (indicated by higher MW) are used, plodding rate is increased, yield stress is increased and plodding generally becomes much steadier.

Thus, the criticality of choosing alkylene glycols of minimum melting point, something completely unrecognized prior to the subject invention, is seen.

Example 14

To further demonstrate the phenomenon noted above, applicants tested the yield stress of various formulations at comparable temperature and results are noted below Processing Data

| | | % Water | Refining Rate (lbs/min) | Plodding Rate (lbs/min) | Process Avg. YS* Temp (F) | Process Yield Stress (kPa) | Avg. Penetration Temp. (F) | Avg. Penetration (mm) | Plodding Comments |
|---|---|---|---|---|---|---|---|---|---|
| | | Formulation Currently Manufactured in Plant | | | | | | | |
| Control | | 5.2 | 9.6 | 9.9 | 85.5 | 276.0 | | | steady |
| | | Formulations Which Have Demonstrated Plant Processability | | | | | | | |
| Ex. 9 | 21% PEG 8000 | 3.2 | 10.4 | 7.6 | 92.4 | 238.7 | | | steady |
| Ex. A | 21% PEG 8000 | 4.0 | 10.5 | 6.5 | 88.8 | 243.3 | | | steady |
| Ex. B | 21% PEG 8000 | 4.5 | 10.2 | 6.2 | 95.3 | 147.0 | 93.3 | 6.7 | steady |
| | | Formulations Which Are Expected to be Plant Processable | | | | | | | |
| Ex. 10 | 26% PEG 8000 | 5.5 | 7.7 | 6.1 | 92.0 | 127.2 | 92.0 | 9.3 | steady |
| Ex. 11 | 21% PEG 3350 | 5.5 | 6.0 | 4.4 | | | 79.4 | 7.6 | slight surging |
| Ex. 12 | 7.0% PEG 4K and 10% PEG 8K | 4.8 | 6.8 | 5.9 | | | 83.5 | 7.9 | slight surging |
| Ex. 13 | 6.5% PEG 4K and 9.3% PEG 8K | 5.1 | 9.4 | 6.8 | | | 88.0 | 7.5 | slight surging |
| | | Formulations Which Are Not Expected to be Plant Processable | | | | | | | |
| Comp 1 | 26% PEG 1450 | 4.5 | 6.5 | 2.5 | 81.3 | 93.4 | | | surging |
| Comp 3 | 25% PEG 1000 | 5.3 | 7.5 | 1.9 | 74.4 | 49.3 | | | slight surging |
| Comp 4 | 26% PEG 600 | 4.5 | 5.3 | 3.0 | 77.0 | 40.7 | | | surging |
| Comp 2 | 26% PEG 300 | 4.3 | 4.3 | 0.9 | 76.1 | 54.2 | | | surging |

*Yield Stress

| | Yield Stress After Aging Formulation Modification | Temp. (F) | Yield Stress (KPa) |
|---|---|---|---|
| Control Formulation Manufactured in Plant | | | |
| Control | | 76.0 | 803.6 |
| Formulations Which Have Demonstrated Plant Processability | | | |
| Ex. 9 (3.2% $H_2O$) | 21% PEG 8000 | 76.0 | 669.7 |
| Ex. 9A (4.0% $H_2O$) | 21% PEG 8000 | 76.0 | 691.0 |
| Formulations Which Are Not Expected to be Plant Processable | | | |
| Comparative 1 | 26% PEG 1450 | 75.0 | 400.4 |
| Comparative 3 | 26% PEG 1000 | 72.0 | 232.8 |
| Comparative 4 | 26% PEG 600 | 73.0 | 142.5 |
| Comparative 2 | 26% PEG 300 | 76.0 | 166.8 |

As clearly noted, the yield stress (measure of hardness) was much higher for formulations with high MP PEG relative to those of lower melting point PEG.

We claim:

1. A detergent bar composition comprising:

(a) 10 to 60% wt. of a synthetic, non-soap detergent;

(b) 20 to 60% wt. of water soluble material which has a melting point in the range 40° C. to 100° C. and which is selected from the group consisting of:

(i) polyalkylene oxide;

(ii) a mixture of polyalkylene oxides; and (iii) block copolymers of polyethylene oxide and polypropylene oxide;

(c) 5 to 50% wt. of water-insoluble material which has a melting point in the range 40° C. to 100° C. and which is fatty acid having carbon chain length of 12 to 24 carbons;

(d) 1 to 14% by wt. water; and (e) 0 to 20% wt. of material which is other than synthetic non-soap detergent and which does not melt below 100° C.;

wherein said compositions are prepared by:

(1) mixing synthetic non-soap detergent (a) and materials (b) and (c) at 50° to 90° C.;

(2) cooling product of step (1) until said product solidifies; and (3) forming said product of step (1) into a bar; said step (3) comprising a milling step.

2. Detergent composition according to claim 1 wherein the quantity of component (a) is 10 to 50% wt.

3. Detergent composition according to claim 1 wherein the quantity of water is 1 to 14.5 wt. %.

4. Detergent composition according to claim 3 wherein the quantity of water is 3 to 12 wt. %.

5. Detergent composition according to claim 1 wherein component (a) is selected from the group consisting of: alkyl ether sulphates; alkylethoxylates; alkyl glyceryl ether sulphonates; alpha olefin sulphonates; acyl taurides; methyl acyl taurates; N-acyl glutamates; acyl isethionates; anionic acyl sarcosinates; alkyl phosphates; methyl glucose esters; protein condensates; ethoxylated alkyl sulphates; alkyl polyglucosides; alkyl amine oxides; betaines; sultaines; alkyl sulphosuccinates, dialkyl sulphosuccinates, acyl lactylates and mixtures thereof.

6. Detergent composition according to claim 1 wherein component (b) comprises one or a mixture of polyethylene glycols having molecular weight from 1500 to 10,000.

7. Detergent composition according to claim 1 wherein component (b) includes polyethylene glycol having molecular weight 50,000 to 500,000 in an amount which is 1 to 4.5% by weight of the composition.

8. Detergent composition according to claim 1 wherein component (c) is selected from the group consisting of lauric, myristic, palmitic, stearic, arachidic and behenic acids and mixtures thereof.

9. Detergent composition according to claim 1 wherein component (e) comprises material selected from the group consisting of starches, kaolin, calcite and mixtures thereof.

10. Detergent composition according to claim 1 which contains less than 10% wt. soap.

11. Detergent composition according to claim 10 wherein component (e) comprises water insoluble soap in an amount from 3% to 10% by weight of the composition.

12. Detergent composition according to claim 11 wherein said soap is the sodium salt of saturated fatty acid having carbon chain lengths of 16 to 22 carbon atoms.

13. Detergent composition according to claim 1 which contains from 5% wt. to 30% wt. fatty acyl isethionate.

14. Detergent composition according to claim 1 wherein is in bar form.

15. A process for the manufacture of a synthetic detergent bar which comprises the steps of:

(i) preparing a liquid mixture comprising:

(a) 10 to 60% wt. of a synthetic, non-soap detergent;

(b) 20 to 60% wt. of water soluble material which has a melting point in the range 40° C. to 100° C. and which is selected from the group consisting of:

(i) polyalkylene oxide;

(ii) a mixture of polyalkylene oxides; and (iii) block copolymers of polyethylene oxide and propylene oxide;

(c) 5 to 50% wt. of water-insoluble material which has a melting point in the range 40° C. to 100° C. and which is fatty acid having carbon chain length of 12 to 24 carbons;

(d) 1 to 14% by wt. water; and (e) 0 to 20% wt. of material which is other than synthetic non-soap detergent and which does not melt below 100° C.;

(ii) cooling the product of step (i) to a temperature at which it solidifies; and (iii) forming the product of step (c) into bars.

16. Process according to claim 15 wherein step (ii) is performed on a chilled, scraped roller.

17. Process according to claim 15 wherein step (iii) comprises milling, plodding and stamping.

18. Process according to claim 15 wherein steps (ii) and (iii) comprise pouring the product of step (i) into molds for bars, and then cooling the said product in the molds so that it solidifies to bars therein.

* * * * *